United States Patent
Van Den Biggelaar et al.

(10) Patent No.: US 8,812,114 B2
(45) Date of Patent: Aug. 19, 2014

(54) LEAD SET FOR NERVE STIMULATOR AND METHOD OF OPERATION THEREOF

(75) Inventors: Johannes F. M. Van Den Biggelaar, Haaren (NL); Jeffrey M. Williams, Andover, MN (US); Marc M. Herregraven, Falcon Heights, MN (US); Paul Edward Sandstrom, Andover, MN (US); Anthony W. Schauer, Hudson, WI (US)

(73) Assignee: Uroplasty, Inc., Minnetonka, MN (US)

( * ) Notice: Subject to any disclaimer, the term of this patent is extended or adjusted under 35 U.S.C. 154(b) by 707 days.

(21) Appl. No.: 11/804,200

(22) Filed: May 17, 2007

(65) Prior Publication Data

US 2008/0039915 A1 Feb. 14, 2008

Related U.S. Application Data

(63) Continuation-in-part of application No. 10/492,578, filed as application No. PCT/US02/33318 on Oct. 18, 2002, now Pat. No. 7,536,226.

(60) Provisional application No. 60/801,589, filed on May 18, 2006, provisional application No. 60/336,074, filed on Oct. 18, 2001.

(51) Int. Cl.
*A61N 1/04* (2006.01)

(52) U.S. Cl.
CPC .................................. *A61N 1/0456* (2013.01)
USPC ............................................ 607/46; 607/149

(58) Field of Classification Search
USPC ........... 607/115–116, 149; 606/129; 600/372, 600/377, 382, 386–392
See application file for complete search history.

(56) References Cited

U.S. PATENT DOCUMENTS 3,893,462 A 7/1975 Manning
3,995,644 A 12/1976 Parsons
(Continued)

FOREIGN PATENT DOCUMENTS

CA 2463936 4/2013
EP 0327304 A1 8/1989
(Continued)

OTHER PUBLICATIONS

Holmes, Rex R., Office action in U.S. Appl. No. 10/492,578, filed Sep. 13, 2004, mailed Jun. 20, 2007, 10 pages.
(Continued)

*Primary Examiner* — Rex R Holmes
(74) *Attorney, Agent, or Firm* — Barbara A. Wrigley; Oppenheimer Wolff & Donnelly LLP

(57) ABSTRACT

Single-use electrical leads for a nerve stimulator are disclosed. The leads include a status flag element such as a fuse, which is deliberately blown after use of the leads has begun to indicate that the leads are not to be reused. The nerve stimulator has a "test mode" that determines a current value for treatment, and a "therapy mode" that administers treatment with the chosen current value. If the fuse in the electrical leads is blown (not conducting), then the stimulator assumes that the leads have already been used and does not enter therapy mode, and optionally may not enter test mode. If the fuse in the electrical leads is intact (conducting), or not blown, then the stimulator assumes that the leads are as yet unused, and allows the user to enter either test mode or therapy mode. The fuse is deliberately blown after a particular amount of time spent in therapy mode. After the fuse is blown, the user may still complete the therapy mode, even though the fuse is non-conducting, although the user may not initiate another therapy mode (and optionally may not initiate another test mode) using the blown leads. Preferably the fuse is electrically isolated from the leads that contact the patient.

14 Claims, 6 Drawing Sheets

(56) References Cited

U.S. PATENT DOCUMENTS

| | | | |
|---|---|---|---|
| 4,406,288 A | 9/1983 | Horwinski et al. | |
| 4,408,609 A | 10/1983 | Axelgaard | |
| 4,519,394 A | 5/1985 | Black et al. | |
| 4,535,785 A | 8/1985 | van den Honert et al. | |
| 4,697,600 A * | 10/1987 | Cardenas et al. | 600/566 |
| 5,056,518 A | 10/1991 | Pethica et al. | |
| 5,094,242 A | 3/1992 | Gleason et al. | |
| 5,562,710 A | 10/1996 | Olsen et al. | |
| 5,573,533 A * | 11/1996 | Strul | 606/34 |
| 5,645,571 A | 7/1997 | Olson et al. | |
| 5,679,022 A | 10/1997 | Cappa et al. | |
| 5,695,495 A | 12/1997 | Ellman et al. | |
| 5,782,892 A | 7/1998 | Castle et al. | |
| 5,857,968 A | 1/1999 | Benja-Athon | |
| 5,906,634 A | 5/1999 | Flynn et al. | |
| 5,951,484 A | 9/1999 | Hoium et al. | |
| 5,954,758 A | 9/1999 | Peckham et al. | |
| 5,976,167 A * | 11/1999 | Lee | 606/189 |
| 6,141,585 A | 10/2000 | Prutchi et al. | |
| 6,233,482 B1 | 5/2001 | Hofmann et al. | |
| 6,493,588 B1 * | 12/2002 | Malaney et al. | 607/46 |
| 6,516,227 B1 | 2/2003 | Meadows et al. | |
| 6,701,190 B2 | 3/2004 | Gliner | |
| 6,904,324 B2 | 6/2005 | Bishay | |
| 7,536,226 B2 | 5/2009 | Williams et al. | |
| 8,046,082 B2 | 10/2011 | Herregraven et al. | |
| 2003/0083729 A1 | 5/2003 | Solosko et al. | |
| 2005/0171576 A1 | 8/2005 | Williams et al. | |
| 2008/0033510 A1 | 2/2008 | Herregraven et al. | |

FOREIGN PATENT DOCUMENTS

| | | |
|---|---|---|
| EP | 2308553 A1 | 4/2011 |
| EP | 1 444 004 B1 | 12/2011 |
| GB | 2 336 214 | 10/1999 |
| WO | WO 97/49453 | 12/1997 |
| WO | WO 99/47204 | 9/1999 |
| WO | WO 03/033068 A2 | 4/2003 |
| WO | 2007136713 A2 | 11/2007 |

OTHER PUBLICATIONS

Holmes, Rex R., Office action in U.S. Appl. No. 10/492,578, filed Sep. 13, 2004, mailed Mar. 14, 2008, 7 pages.

Holmes, Rex R., Office action in U.S. Appl. No. 10/492,578, filed Sep. 13, 2004, mailed Jun. 24, 2008, 9 pages.

Uroplasty, Inc., Urgent PC Neuromodulation System, Urgent PC Stimulator Instructions for Use, 2005, pp. 14-17.

Interstitial Cystitis Network, "Urosurge's PercSANS receives FDA approval for frequency, urgency & more," Interstitial Cystitis Newsletter, Feb. 10, 2000, 6 pages.

Japan External Trade Organization, "Health Care '97 brings Midwest firms face-to-face with success," JETRO Midwest Newsletter, Jul./Aug. 1997, 4 pages.

Stoller, Marshall, "SANS—Stoller afferent nerve stimulation for frequency, urgency and incontinence," Interstitial Cystitis Network—Chat Log (www.ic-network.com), Mar. 7, 2000, 6 pages.

University of Iowa, "New treatment for urinary incontinence at UI receives FDA approval," University of Iowa Health Care News, Feb. 28, 2000, 2 pages.

U.S. Appl. No. 60/336,074, filed Oct. 18, 2001 (J. Williams, et al., "Neuromodulation of the Posterior Tibial nerve, Apparatus, System and Protocol for Treatment of Urinary Disorders").

U.S. Appl. No. 60/801,589, filed May 18, 2006 (J. F. M. van den Biggelaar, et al., "Nerve Stimulator").

USPTO, Notice of Allowance in U.S. Appl. No. 10/492,578, Dec. 30, 2008, 8 pages.

USPTO, Office Action in U.S. Appl. No. 10/492,578, Jun. 20, 2007, 10 pages.

USPTO, Office Action in U.S. Appl. No. 10/492,578, Mar. 14, 2008, 7 pages.

USPTO, Office Action in U.S. Appl. No. 10/492,578, Jun. 24, 2008, 9 pages.

Williams, Jeffrey M., Reply to Office Action in U.S. Appl. No. 10/492,578, Nov. 20, 2007, 21 pages.

Williams, Jeffrey M., Reply to Office Action in U.S. Appl. No. 10/492,578, Aug. 19, 2008, 26 pages.

Williams, Jeffrey M., Request for Continued Examination in U.S. Appl. No. 10/492,578, Jun. 16, 2008, 17 pages.

Uroplasty, Inc., Urgent(R) PC Stimulator: Instructions for Use, Oct. 2005, pp. 14-17.

European Patent Office, Supplementary European Search Report for European Application No. 07 794 997.2, Dec. 14, 2009, 6 pages.

SANS Examine the revolutionary SANS(TM) device at EAU Stand 9.05., UroSurge (1998).

SANS "Introducing an innovative point of treatment for urge incontinence," UroSurge (1998).

SANS "Introducing two New Treatments for Stress and Urge Incontinence," UroSurge (1998).

SANS "Bold innovations in urology. Visit UroSurge at the EAU Convention.," UroSurge (1998).

"Sacral Nerve Stimulation Improves Chronic Voiding Dysfunction Systems," Medtronic (Undated but on record at USPTO as of Aug. 13, 2004).

Stoller, M.L., "Needle Stimulation (through the skin) for the Treatment of Incontinence," Quality Care, vol. 16, No. 1 (Winter 1998), pp. 1-2 (mailed Feb. 1998).

Stoller, M.L., et al ., "The Efficacy of Acupuncture in Reversing the Unstable Bladder in Pig-Tailed Monkeys," O Am Urological, (1998).

Bolz, A., "Die Bedeutung Der Phasengrenze Zwischen Alloplastischen Festkorpem Und Biologischen Geweben Fur Die Elektrostimulation," pp. 11-15 (Feb. 1995).

Urbasvek, A., "Konzeption Und Technische Losungen Zur Optimierung Der Frequenzadaptiven Elektrostimulation Des Herzens," pp. 23-25, (May 1995).

Cystomedix, Inc., Reply to Office Action, European Patent Application No. 02 786 437.0, Dec. 16, 2008, 24 pages.

Cystomedix, Inc., Reply to Office Action, European Patent Application No. 02 786 437.0, Aug. 12, 2009, 12 pages.

European Patent Office, Office Action, European Patent Application No. 02 786 437.0, Aug. 8, 2008, 7 pages.

European Patent Office, Office Action, European Patent Application No. 02 786 437.0, Feb. 19, 2009, 3 pages.

European Patent Office, Supplementary Partial European Search Report, European Patent Application No. 02 786 437.0, Jun. 16, 2006, 5 pages.

International Preliminary Examining Authority/US, International Preliminary Examination Report, International Patent Application No. PCT/US02/33318, Aug. 8, 2003, 3 pages.

International Searching Authority/US, International Search Report, International Patent Application No. PCT/US02/33318, Apr. 23, 2003, 4 pages.

International Searching Authority/US, International Search Report, International Patent Application No. PCT/US07/11847, Aug. 22, 2008, 2 pages.

International Searching Authority/US, Written Opinion of the International Searching Authority, International Patent Application No. PCT/US07/11847, Aug. 22, 2008, 3 pages.

Uroplasty, Inc., Reply to Supplementary Search Report, European Patent Application No. 07 794 997.2, Feb. 26, 2010, 9 pages.

Cystomedix, Inc., Reply to Extended European Search Report: European Patent Application No. 10185417.2, Oct. 11, 2011, 19 pages.

European Patent Office, Extended European Search Report: European Patent Application No. 10185417.2, Feb. 18, 2011, 10 pages.

Canadian Patent Office, Office Action: Canadian Patent Application No. 2,463,936, Jul. 19, 2010, 4 pages.

Cystomedix, Inc., Reply to Office Action: Canadian Patent Application No. 2,463,936, Jan. 19, 2011, 39 pages.

United States Patent and Trademark Office, Office Action: U.S. Appl. No. 12/685,557, Jan. 20, 2011, 29 pages.

Herregraven, Marc et al., Reply to Office Action: U.S. Appl. No. 12/685,557, Apr. 20, 2011, 15 pages.

(56) References Cited

OTHER PUBLICATIONS

United States Patent and Trademark Office, Notice of Allowance and Fee(s) Due: U.S. Appl. No. 12/685,557, Jun. 22, 2011, 24 pages.

European Patent Office, Office Action: European Patent Application No. 07 794 997.2, Jun. 25, 2012, 4 pages.

Canadian Patent Office, Office Action: Canadian Patent Application No. 2,463,936, Jan. 3, 2012, 3 pages.

Uroplasty, Inc. Reply to Office Action: Canadian Patent Application No. 2,463,936, Jul. 3, 2012. 5 Pages.

European Patent Office. Communication Under Rule 71(3) EPC, European Patent Application No. 10 185 4171, May 2, 2013. 25 pages.

European Patent Office. Communication Under Rule 71(3) EPC, European Patent Application No. 10 185 4171, Oct. 25, 2013. 25 Pages.

European Patent Office. Communication Under Rule 71(3) EPC, European Patent Application No. 02 786 437.0, Jun. 7, 2011. 30 Pages.

European Patent Office. Noting of Loss of Rights Pursuant to Rule 112(1) EPC, European Patent Application No. 07 794 997.2, Feb. 13, 2013. 1 Page.

Uroplasty, Inc. Reply to Communication Under Rule 71(3) EPC, European Patent Application No. 10 185 417.2, Aug. 29, 2013. 4 Pages.

\* cited by examiner

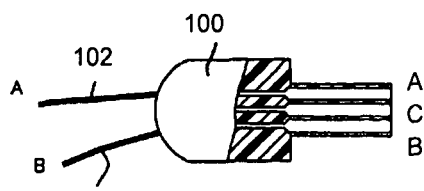
FIG. 6
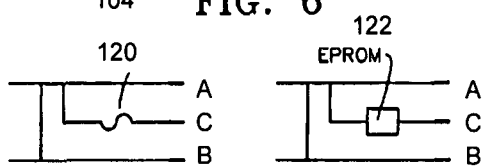
FIG. 7    FIG. 8
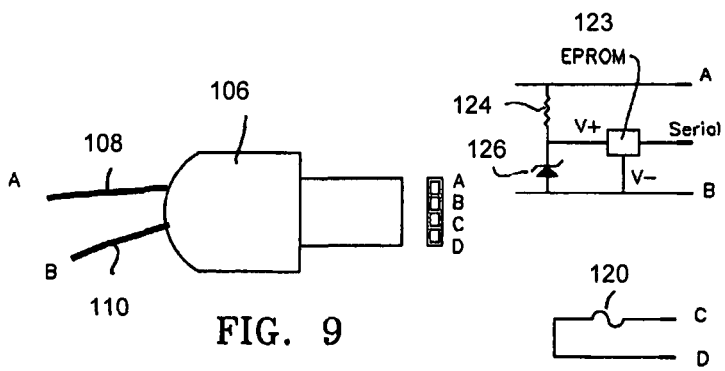
FIG. 9
FIG. 10
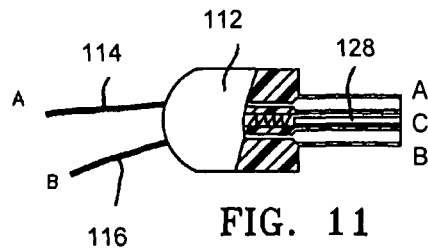
FIG. 11

LEAD SET FOR NERVE STIMULATOR AND METHOD OF OPERATION THEREOF

CROSS-REFERENCE TO RELATED APPLICATIONS

This application claims the benefit of U.S. Provisional Patent Application Ser. No. 60/801,589 filed May 18, 2006, which hereby is incorporated herein in its entirety by reference thereto. This application is a continuation-in-part of and claims the benefit of U.S. patent application Ser. No. 10/492,578 filed Sep. 13, 2004 now U.S. Pat. No. 7,536,226, which hereby is incorporated herein in its entirety by reference thereto, and which is National Stage Entry of PCT/US02/33318 filed Oct. 18, 2002, which claims the benefit of U.S. Provisional Patent Application Ser. No. 60/336,074 filed Oct. 18, 2001.

STATEMENT REGARDING FEDERALLY SPONSORED RESEARCH OR DEVELOPMENT

Not Applicable

BACKGROUND OF THE INVENTION

1. Field of the Invention

The present invention is directed to nerve stimulators, and more particularly to electrical leads for nerve stimulators and methods of operation thereof.

2. Description of the Related Art

Physical therapists, chiropractors, and other medical providers have used nerve and muscle stimulation to treat a variety of ailments. These medical providers have used electronic muscle stimulation (EMS) and transcutaneous electrical nerve stimulation (TENS) as a treatment for muscle and joint rehabilitation as well as chronic pain. Urologists and obstetrician/gynecologists have used a form of TENS for pelvic floor stimulation to treat incontinence and pelvic pain. In addition, medical providers have used a variety of implantable and percutaneous stimulators to manage pain, to create local nerve blocks, and to treat incontinence, Parkinson's disease, and multiple sclerosis.

Transcutaneous stimulators, i.e., stimulators which do not physically penetrate the skin surface, are less invasive than percutaneous and implantable stimulators. However, transcutaneous stimulators often require higher current levels than percutaneous and implantable stimulators. Higher current levels can cause irritation and discomfort when used for extended periods. Also, since transcutaneous stimulators stimulate on the skin surface, their target site usually covers a large area. Thus, transcutaneous stimulators may not be highly effective for direct nerve stimulation.

More typically, providers use implantable stimulators when there is a need for direct nerve stimulation or continuous stimulation. Implantable stimulators can free a patient from the need for constant and frequent manual treatment. However, implantable stimulators can cause mild discomfort, and often cause more severe implant-site pain.

Percutaneous stimulators provide direct nerve stimulation without the invasiveness of an implant. During treatment, a conducting needle is inserted to provide electrical stimulation to a target nerve. The needle is electrically connected to a controller by a series of leads, often bound together at one end as a cable that connects to the controller.

Leads for percutaneous stimulators may be designated for single-use only, particularly if they have not been tested or validated for multiple uses. Since such leads should not be used multiple times, there exists a need for electrical leads that ensure against multiple uses and for a method of operation with these single-use leads.

BRIEF SUMMARY OF THE INVENTION

An embodiment is a lead set for a nerve stimulator, comprising a keyed connector block having first, second, third and fourth conductors; a first lead extending from the first conductor of the connector block and terminating in a patch electrode having adhesive on a surface thereof; a second lead extending from the second conductor of the connector block and terminating in a needle clip; and a fuse disposed in the connector block, the fuse being connected between the third and fourth conductors.

Another embodiment is a lead set for a nerve stimulator, comprising a keyed connector block; a first lead extending from the connector block and terminating in a patch electrode; a second lead extending from the connector block and terminating in a needle clip; and a fuse disposed in the connector block and electrically isolated from both the first lead and the second lead.

Another embodiment is a lead set for a nerve stimulator, comprising a keyed connector block having first, second, third and fourth conductors; a first lead extending from the first conductor of the connector block and terminating in a patch electrode having adhesive on a surface thereof; a second lead extending from the second conductor of the connector block and terminating in a needle; and a fuse disposed in the connector block, the fuse being connected between the third and fourth conductors. The needle and the patch electrode may be permanently or removably connected to their leads.

Another embodiment is a method for stimulating a nerve, comprising executing a test mode to determine an initial therapy current level; executing a therapy mode to deliver a current to the nerve through a lead set having a status flag element, the current being initially set to the initial therapy current level; and setting the status flag element in the lead set within a predetermined time after beginning execution of the therapy mode.

Another embodiment is a method for stimulating a nerve of a patient with therapy current, comprising activating a stimulator, the stimulator comprising a handheld controller coupled to a lead set having a fuse disposed therein; entering a test mode; adjusting a test current during test mode to set a final test current level; exiting the test mode; entering a therapy mode when the test mode is exited; forming an initial therapy current level from the final test current level; providing a therapy current through the lead set; blowing the fuse within a predetermined time after entering therapy mode; and exiting the therapy mode within a predetermined time after the fuse is blown.

BRIEF DESCRIPTION OF THE SEVERAL VIEWS OF THE DRAWINGS

FIG. 6 is a partial cross-sectional view of a three port single-use connector.

FIG. 7 is an electrical schematic for a fuse implementation of the single-use connector of FIG. 6.

FIG. 8 is an electrical schematic for an EPROM implementation of the single-use connector of FIG. 6.

FIG. 9 is a plan view of a four port single-use connector.

FIG. 10 is an electrical schematic for an EPROM and fuse implementation of the single-use connector of FIG. 9.

FIG. 11 is a partial cross-sectional view of a mechanical three port single-use connector.

DETAILED DESCRIPTION OF THE INVENTION

Nerve and muscle stimulation may be used by medical providers to treat a variety of ailments. For instance, urinary incontinence may be treated by stimulating the sacral nerves, which affect bladder control. One such treatment may be done in a percutaneous manner by inserting a fine gauge needle into the posterior tibial nerve just above the ankle and applying an electrical stimulation to the needle. The tibial nerve carries the electrical stimulation up the leg to the S3 region of the lower spinal cord. Electrical stimulation near the S3 region is effective in treating chronic pelvic pain, fecal incontinence, nocturnal urinary frequency, interstitial cystitis symptoms of urinary frequency, urinary urgency, and urinary urge incontinence, and overactive bladder symptoms of urinary frequency, urinary urgency and urinary urge incontinence.

An example of an electrical nerve stimulator is disclosed in U.S. Pat. No. 6,493,588 entitled "Electro-nerve stimulator systems and methods," which issued Dec. 10, 2002 to Malaney et al., and which is hereby incorporated herein in its entirety by reference thereto. The electrical leads for the stimulator disclosed in Malaney et al. are capable of being reused.

One example of suitable single-use leads rely on the conductivity between two particular electrical connections to determine if the lead set have been used. The two particular connections have a fuse between them that conducts electricity prior to use. Once a particular set of criteria is met that determines that the lead set should not be reused, the fuse is deliberately blown, and the two particular connections no longer conduct electricity from one to the other. The two particular connections are coupled to a controller that can sense the conductivity between them and can also generate enough current to blow the fuse when required. Preferably, the fuse and the electrical connections to the fuse are electrically isolated from the leads that deliver the stimulation current, although they may be combined with the stimulation current leads if desired.

Figure 1:
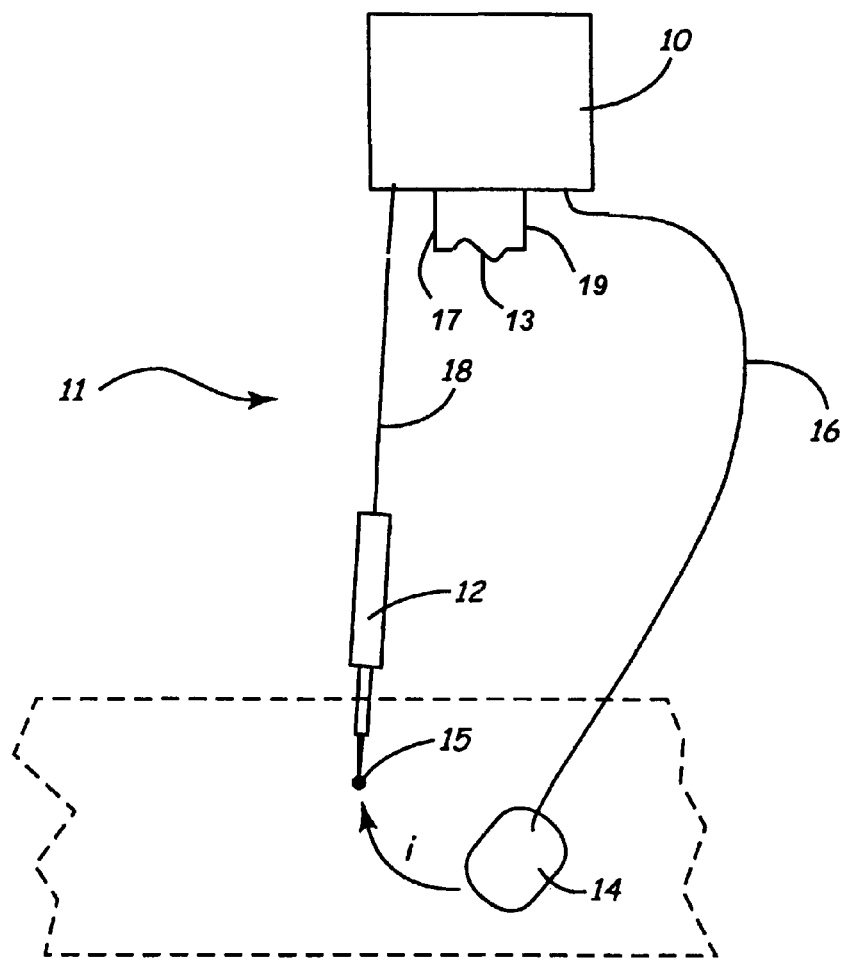
FIG. 1 is a schematic view of a nerve stimulator in use on a patient.

FIG. 1 shows an exemplary nerve stimulator 11 that has a set of single-use electrical leads. The leads are shown in FIG. 1 as individual wires emerging from a controller 10, although it will be understood that any or all of the leads may be packaged in a connector to simplify connecting or removing the leads from the controller 10.

The controller 10 may include circuitry for monitoring time and generating a prescribed amount of current. The current may be AC, DC, or may alternatively be pulsed. The controller 10 may also include a battery or may alternatively use an external source of power.

As shown in FIG. 1, the controller 10 has four electrical connections or leads, although it may alternatively have more or fewer electrical connections, such as 3, 5, 6 and so forth. In the example of FIG. 1, two leads 16 and 18 provide a current through a portion of the patient's body, and the other two leads 17 and 19 are used for ensuring that the electrical leads are used for only a single therapy session.

Lead 16 connects the controller 10 to a transcutaneous electrode 14 that is placed in a suitable location on the exterior of the patient's body. The electrode 14 may be conductive or one or both sides, and may optionally have an adhesive that sticks to the patient's body.

Lead 18 connects the controller 10 to a percutaneous electrode needle 12 that is inserted into the patient's body at a stimulation site 15 and connects electrically near a nerve or bundle of nerves to be stimulated. The connector generates a voltage difference between leads 16 and 18, so that current flows between the electrode 14 and the needle 12. This current is denoted as arrow "i" in FIG. 1.

The remaining two leads 17 and 19 are connected to a fuse 13. The controller contains circuitry that can sense whether or not fuse 13 is blown, by generating a relatively small voltage between leads 17 and 19 and sensing whether or not any current is flowing through leads 17 and 19. The controller also contains circuitry that can deliberately blow the fuse 13, by generating a relatively large voltage between leads 17 and 19. The voltages used in leads 17 and 19 are determined in part by the fuse 13, and are typically low enough to not damage any tissue if it should come in contact with the leads 17 or 19.

Figure 2:
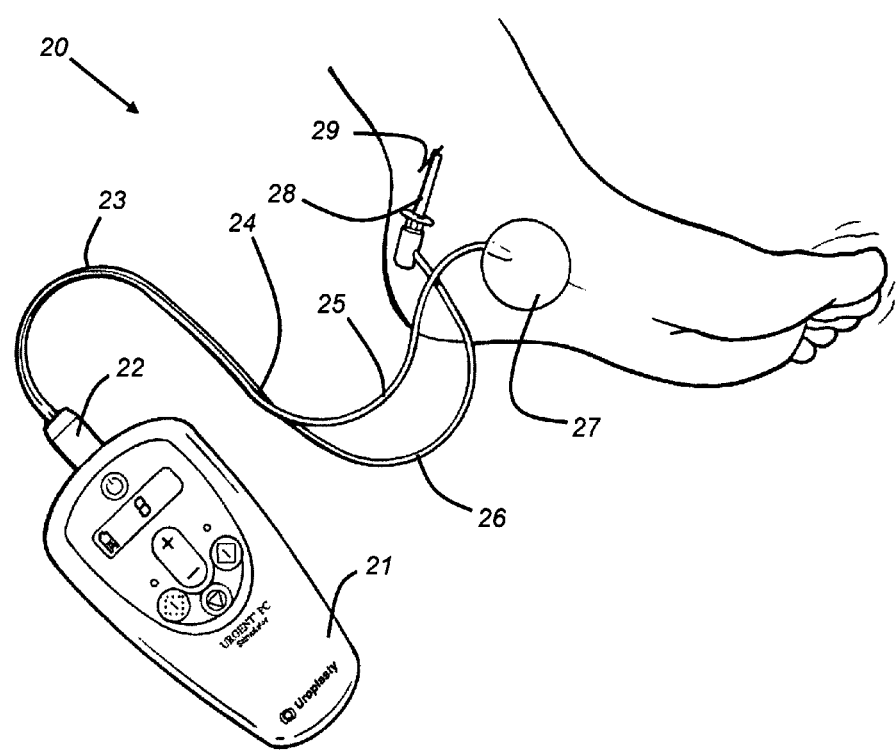
FIG. 2 is a perspective view of a nerve stimulator in use on a patient.

Illustratively, the fuse 13 and the electrical leads 16, 17, 18 and 19 are bundled together at the controller 10 and connect to the controller 10 through a connector. A simulator 20 having an exemplary connector 22 is shown in FIG. 2, along with typical a controller unit 21, leads 25 and 26, an electrode 27, and a clip 28 that attaches to a needle 29. These elements are described in greater detail below. The descriptions in the following paragraphs are merely exemplary.

The controller unit 21 may be a portable unit, with a lightweight, ergonomic, handheld design. The controller unit 21 may have electronic touch pad controls or other suitable buttons or switches for entering data or changing the status of the controller unit 21. For instance, the controller unit 21 may have raised and embossed buttons, which provide tactile feedback to the user while protecting the controller unit 21 from moisture, contamination, and so forth. It will be readily understood by one of ordinary skill in the art that the controller may use any combination of buttons, switches, joysticks, levers, or any other suitable adjustment mechanism. The controller unit 21 may have a display such as an LCD screen for providing operational status and visual feedback information to the user.

The controller unit 21 includes a connection site to mate with a connector 22. The connection site may be a one-way fit connection site to ensure that the connector 22 for the leads cannot be plugged in backwards. The connector 22 may be keyed to the connection site in any desired manner, such as extended ribs, chamfers, spacing of the pins or sockets, and so forth.

The controller unit 21 contains the electronics suitable for providing a current for stimulating the desired nerve in the patient. Although specific current settings are described in the following paragraph, it will be understood that any suitable current scheme may used, such as direct current ("DC"), alternating current ("AC") with a continuously varying current, AC with a pulsed current, or a combination of any of these. The specific current settings in the following three paragraphs are merely exemplary.

The controller unit 21 may have twenty current setting levels, ranging from level "0" to level "19", representing a current range of 0 mA to approximately 9 mA. At level "0", the device produces 0 mA current. At level "1", the current is 0.15 mA. At level "2", the current level is 0.5 mA, and so forth. Each subsequent level represents a 0.5 mA increase. It will be understood that other increments and levels may be used as well.

The controller unit 21 may provide a pulsed current. The frequency of the pulses may be fixed at 20 Hz. The pulse width may be 200 microseconds. The pulse waveform may be square. It will be understood that other suitable frequencies, pulse widths, and waveforms may be used as well, and may optionally be adjustable.

The internal resistance of the controller unit 21 may be varied by the controller unit 21 from 500 to 4000 Ohms in order to provide the desired current. This range is merely exemplary, and other suitable ranges may be used as well.

The following paragraphs describe the buttons on the controller unit 21 in greater detail. These descriptions are merely exemplary.

The controller unit 21 may have a "power" button that turns the power on or off. To turn the power on or off, the user may be required to depress the power button for an extended period, such as approximately two seconds, to protect the controller unit 21 from inadvertent status changes.

The controller may have a "test" button, which begins "test mode". "Test mode" is described in greater detail later in this document. Upon entering test mode, the default current setting may be "0", or 0 mA. At the completion of the test mode, the final current setting may be the baseline setting in "therapy mode", which is also described in greater detail later in this document. To activate test mode, the user may be required to depress the test mode button for an extended period, such as approximately two seconds. This may protect the controller unit 21 from inadvertent status changes.

The controller unit 21 may have a "therapy" button, which begins "therapy mode". The default current setting for therapy mode may be the final current setting in test mode. However, the current adjustment button (described below) may be used to increase or decrease the level at any time. To activate therapy mode, the user may be required to depress the therapy mode button for an extended period, such as approximately two seconds. This may protect the controller unit 21 from inadvertent status changes.

The controller unit 21 may have a "stop" button that stops the flow of current in test or therapy mode. If treatment is stopped or interrupted during therapy mode, the remaining therapy mode time may be displayed. Once stopped, the treatment session may need to be restarted, beginning with test mode.

Finally, the controller unit 21 may have a "current adjustment" button, which increases or decreases current. The current may be adjustable in both test and therapy modes.

The following seven paragraphs describe the status screen on the controller unit 21 in greater detail, which may have icons and/or alpha-numeric characters that provide operational feedback. These descriptions are merely exemplary.

The controller unit 21 may have a "battery level" icon. The number of horizontal lines displayed in the battery level icon may represent the remaining battery life. Seven horizontal lines may indicate a fully charged battery whereas one horizontal line may indicate that the battery is nearly empty. A flashing battery level icon may signal that a replacement battery may be needed. In addition, the controller unit 21 may emit a periodic beep when the battery is nearly empty, such as when only one line is displayed in the battery level icon. The controller unit 21 may be designed to prohibit the start of test mode if there is insufficient battery life remaining to complete the treatment.

The controller unit 21 may have a "lead wire status" icon, which may indicate the functional status of the lead wire. The icon may flash if a new lead wire is required.

The controller unit 21 may have an "inactive current" icon, which may indicate that current is not flowing through the lead set. This icon may signal that the user should check the security of the lead connector, the adherence of the surface electrode, and the placement of the needle electrode clip.

The controller unit 21 may have an "active current" icon, which may indicate that current is actively flowing through the lead set.

The controller unit 21 may have a "service required" icon. If a fault is detected, therapy mode may end and the service required icon may appear on the screen.

The controller unit 21 may have a "treatment status" portion of the screen. During test mode, the word "TEST" may appear on the screen. Once therapy mode is started, a countdown timer may appear in a portion of the display. This timer may indicate how much time is left in the therapy session. Upon completion of therapy, the word "END" may flash on the screen until shutdown.

Finally, the controller unit 21 may have a "current setting" portion of the screen, which may display the selected current setting. The current may be adjustable in both test and therapy modes.

The leads transfers the electrical current from the controller unit 21 to the tibial nerve and may include one or more lead sets such as lead set 23, one or more percutaneous electrodes such as needle electrode 29, one or more surface electrodes such as electrode 27, and an optional alcohol pad (not shown). The following description of these elements is merely exemplary.

The components of the lead set 23 create the non-sterile circuit interface between the controller unit 21 and the patient. A one-way fit connector 22 is attached to the proximal end of the lead wire 23. The distal end of the lead wire may be split into individual wires 25 and 26, with the split occurring at a fork 24. One wire 25 may be attached to an adhesive-backed surface electrode 27; the other wire 26 may be attached to a needle electrode clip 28.

The needle electrode clip 28 clips to the needle electrode 29. The needle electrode 29 illustratively is a 34 gauge solid stainless steel needle, which may be packaged within a plastic guide tube with stop plug. Each needle electrode 29 may be supplied sterile (ethylene oxide) in an individual peel-open package.

The alcohol pad may be prepackaged to clean the needle electrode insertion site.

The following paragraphs describe a preferred set of instructions for use of the stimulator. These instructions are merely exemplary. Any suitable instructions may be used.

Percutaneous tibial nerve stimulation (PTNS) therapy involves placing the needle electrode 29 into the lower, inner aspect of either leg slightly cephalad to the medial malleolus. The surface electrode 27 is placed over the medial aspect of the calcaneous on the same leg. The lead set 23 first is plugged into the stimulator 21, and then the needle electrode clip 28 is clipped to the needle electrode 29. The stimulator 21 produces an adjustable electrical pulse that travels to the sacral nerve plexus via the tibial nerve. Among other functions, the sacral nerve plexus regulates bladder and pelvic floor function.

The patient is typically treated once per week for 30 minutes for a period of 12 weeks. No decision to discontinue treatment should be made until the patient completes the 12 treatments. For patients responding to treatment, the time between treatment sessions may be slowly increased after the initial 12 treatments, with the patient closely monitored for the return of symptoms. If symptoms reappear or increase in severity, the patient's treatment schedule should revert to the last previously effective treatment schedule. The treatment length of 30 minutes and period of 12 weeks are merely exemplary, and any suitable length and period may be used.

Figure 3:
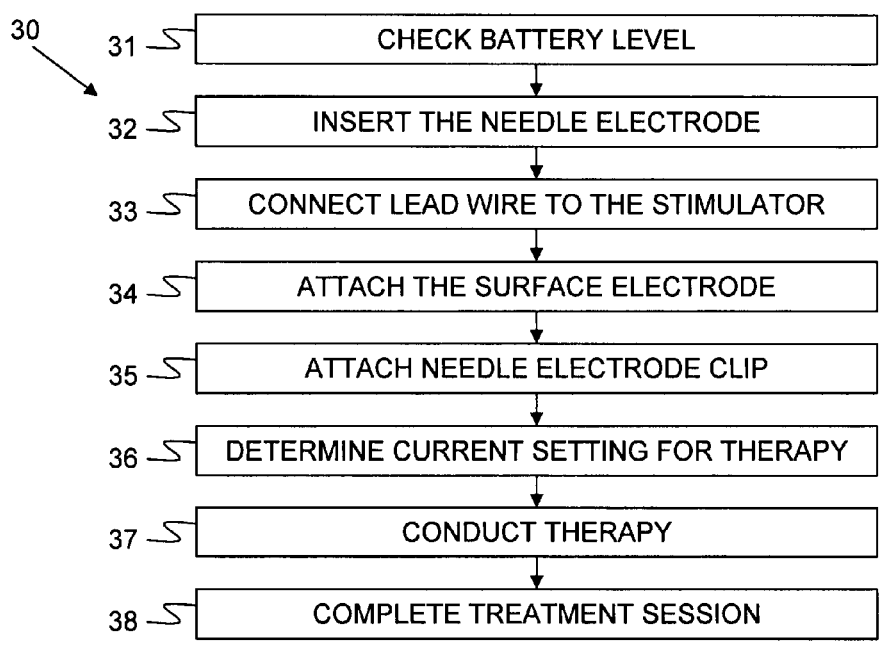
FIG. 3 is a flow chart of the operation of a nerve stimulator.
Figure 4:
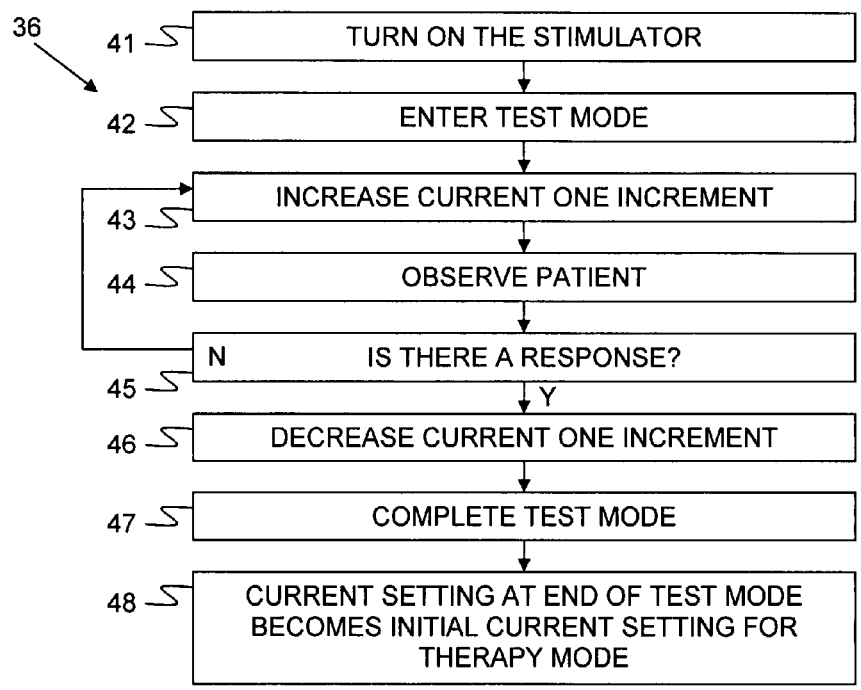
FIG. 4 is a flow chart of a current determining operation for a nerve stimulator.
Figure 5:
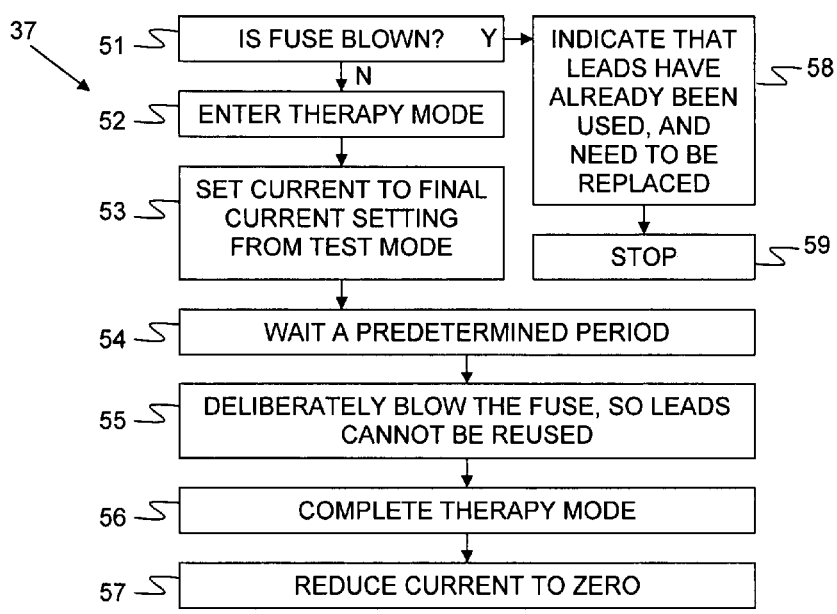
FIG. 5 is a flow chart of a therapy mode for a nerve stimulator.

The following section describes a preferred treatment protocol 30 for each treatment session, shown as flow charts in FIGS. 3-5. Because the protocol is lengthy, it is divided into sections numbered 1-8, with appropriately lettered subsections. The described protocol is merely exemplary. Alternatively, any suitable protocol may be used.

1. Check Battery Level (Block 31)

Before beginning any treatment session, it is advisable to check the battery level. To check the battery level, turn on the stimulator by pressing and holding the power button for approximately 2 seconds. An audible tone will sound and icons will appear on the screen. Battery replacement is recommended when there is only one line remaining in the battery level icon. To conserve battery power, the stimulator may be turned off during patient preparation. Note that the system is designed to prohibit the start of Test mode if there is insufficient battery life remaining to complete the treatment.

2. Insert the Needle Electrode (Block 32)

Locate the insertion site for the needle electrode by identifying the location on the lower inner aspect of either leg that is approximately three fingerbreadths (5 cm or 2 inches) cephalad to the medial malleolus and approximately one fingerbreadth (2 cm or ¾ inch) posterior to the tibia.

To prepare the needle electrode insertion site, open the lead set packaging. Remove and open the alcohol pad. Use the alcohol pad to clean the skin area surrounding the identified insertion site.

Place the patient in a comfortable position, supine or sitting, for easy access to the insertion site; for example, the patient may sit with the soles of the feet together and knees abducted and flexed. Open the sterile needle electrode package and remove the needle electrode/guide tube assembly.

Place the needle electrode/guide tube assembly over the identified and cleaned insertion site in a position that creates a 60-degree angle between the needle electrode and the ankle. Remove the stop plug in the guide tube to release the needle electrode.

Gently tap the needle electrode head to pierce the skin. Once the needle electrode has penetrated the skin, remove the guide tube and advance the needle electrode using a rotating motion to facilitate entry. Note: it is preferable to maintain a 60-degree angle with the needle electrode while advancing it in a path that is parallel to the tibia. When appropriately inserted, about half of the tip of the needle electrode will be inserted in the leg, with about 2 cm (¾ inch) left exposed.

3. Connect Lead Wire to the Stimulator (Block 33)

Plug the one-way fit connector of the lead set into the stimulator's connection site. Verify that the one-way fit connector is inserted correctly.

4. Attach the Surface Electrode (Block 34)

Remove the adhesive backing from the surface electrode.

Place the surface electrode near the medial aspect of the calcaneous on the same leg as the needle electrode insertion.

5. Attach Needle Electrode Clip (Block 35)

Depress the plunger on the needle electrode clip to expose the connection hook at the tip. Loop the connection hook around the needle electrode and release.

6. Determine Current Setting for Therapy (Block 36)

Turn on the stimulator by pressing and holding the power button for approximately 2 seconds (FIG. 4, block 41). An audible tone will sound and symbols will appear on the screen. Note that if the lead wire status icon is blinking, ensure that the lead set connector is secure in the stimulator's connection site.

Enter test mode by pressing and holding the test button for approximately 2 seconds (block 42). The default setting for test mode is level 0 (0 mA current). Note that if the inactive current icon appears, current is not flowing through the lead set. Check the security of the lead wire connector, the adherence of the surface electrode, and the placement of the needle electrode clip.

Using the current adjustment button, slowly increase the current (block 43) while observing the patient's foot for a response (blocks 44 and 45). Patient response is generally a toe flex or fan, or an extension of the entire foot.

Once a patient response is observed, reduce current setting by one level (block 46) to complete test mode (block 47), and begin therapy mode (block 48).

If the incremental adjustment of amplitude fails to elicit toe flex or fan, press the stop button and reposition the needle electrode slightly. Re-enter test mode using the preceding procedure.

If repositioning the needle electrode and repeating the current step-up procedure fails to elicit patient response, discard the needle electrode. Open the second needle electrode included with the lead set and repeat the procedure on the other leg.

7. Conduct Therapy (Block 37)

After completing test mode, therapy mode can be entered by either (i) pressing the stop button to end test mode and then pressing the therapy button to start therapy mode; or (ii) pressing the therapy button while the test mode is still active. Note that the test mode is a prerequisite to therapy mode.

For optimal treatment, the default current setting for therapy mode should be the final current setting in test mode. However, the current adjustment button can be used to increase or decrease the current level at any time during Therapy mode.

Therapy mode time is automatically set for 30 minutes.

When the therapy time has elapsed, therapy mode automatically ends the current becomes inactive (block 57) and the stimulator emits a series of three beeps.

8. Complete Treatment Session (Block 38)

Turn off the stimulator by holding down the power button for approximately 2 seconds.

Remove the needle electrode clip from the needle electrode.

Using a smooth, fluid motion, quickly remove the needle electrode and surface electrode from the leg. If bleeding occurs, apply slight pressure and bandage.

Disconnect the lead set from the stimulator and properly dispose of the lead set components. The treatment session is now complete.

Treatments as described above are preferably administered periodically over a prescribed length of time. For instance, the treatments may include 12 sessions, typically once per week. After the initial 12 treatments, the time between treatments may slowly increase, with the patient closely monitored for the return of symptoms. If symptoms reappear or increase in severity, the patient's treatment schedule may revert to the last previously effective treatment schedule.

It will be beneficial to reiterate and summarize several of the points from the exemplary protocol above, especially "test mode" and "therapy mode." In general terms, "test mode" is used to determine a current value for treatment, and "therapy mode" administers treatment with the chosen current value. More specific aspects of these two modes are presented in the following paragraphs.

Refer to FIG. 5. If the fuse in the electrical leads is blown, that is, not conducting (block 51 yes), then the controller assumes that the leads have already been used (block 58). The controller produces a suitable signal, such as an audible beep or a visual cue on its display indicating that the leads need to be replaced. The controller does not enter test mode or therapy mode at this point. Alternatively, the controller may enter test mode but not therapy mode.

If the fuse in the electrical leads is intact (conducting), or not blown, then the controller assumes that the leads are as yet unused, and allows the user to enter either test mode or therapy mode.

Refer now to FIG. 4. Once inside test mode (block 42), the user may manually step up the current (blocks 43, 44 and 45) until the patient's foot shows a response, such as a movement. Once a response is seen, the user may manually decrease the current by one increment (block 46) to a value that is to be used as a default in therapy mode. Test mode lasts for a particular amount of time, such as five minutes, then shuts off. The user can also manually exit test mode before the particular time expires. The user can exit and enter test mode an unlimited number of times, as long as the fuse in the leads is conducting. Entering or exiting test mode does not cause the controller to deliberately blow the fuse. Alternatively, the fuse may be blown after a predetermined number of test mode reentries.

Refer again to FIG. 5. Once a default current value is determined from test mode (block 53; see also block 48 in FIG. 4) the user then begins therapy mode. The current may be increased or decreased at any time in therapy mode, although preferably the current remains fairly close to the default value for the full extent of therapy mode. Therapy mode may last for a fixed amount of time, although the user can exit at any time. Unlike test mode, therapy mode triggers the deliberate blowing of the fuse in the leads (block 55) thereby ensuring that the leads are not reused after the therapy mode ends. The fuse may be blown after a particular amount of time spent in therapy mode (block 54) such as one minute, two minutes, five minutes or any other suitable time interval. After the fuse is deliberately blown, the user may still complete the therapy mode (block 56) even though the fuse is non-conducting, although the user may not initiate another test mode or therapy mode using the blown leads. Alternatively, the user may initiate a test mode but not a therapy mode using the blown leads. Once therapy mode ends, the current is set to zero (block 57).

The nerve stimulation system is effective not only for the treatment of chronic pelvic pain, fecal incontinence, nocturnal urinary frequency, interstitial cystitis symptoms of urinary frequency, urinary urgency, and urinary urge incontinence, and overactive bladder symptoms of urinary frequency, urinary urgency and urinary urge incontinence, but may also be effective for both nerve and muscle stimulation to treat other numerous conditions, including, for example, muscle and joint rehabilitation, chronic pain, Parkinson's disease, obesity, and multiple sclerosis. While many of these other conditions may use different nerve pathways than the one described herein, the nerve stimulator may be used in a similar manner for any suitable nerve pathway in the body. In addition, the system may be used to manage pain and create local nerve blocks, as well as in any other application in which it is desirable to provide electrical nerve and/or muscle stimulation.

Although a fuse is a simple and effective way to indicate whether the lead set has been used, other means may be used as well. Generally, the lead set may contain a "status flag" element to indicate whether the lead set has been used. The status flag element is reset by default at "use," and once a particular set of criteria is met that determines that the leads should not be reused, the status flag element is set at "do not use." The controller senses the lead set status as indicated by the status flag element, and is also capable of setting the status flag element at "do not use" when required.

A variety of electrical and mechanical techniques for implementing a status flag element are described in U.S. Patent Application Publication No. US 2005/0171576 published Aug. 4, 2005, which hereby is incorporated herein in its entirety by reference thereto. Illustrative techniques include the following.

FIGS. 6-11 illustrate a variety of possible techniques which may be implemented in a connector for ensuring single use. As shown in FIG. 6, a connector 100 includes two ports A and B corresponding to stimulation current lead wires 102 and 104 (also designated by corresponding reference letters A and B). FIG. 7 shows one type of status flag, illustratively a fuse 120, which may be blown and subsequently sensed by a controller (not shown) through a third port C to indicate that the lead set has been used. Alternatively, as illustrated in FIG. 8, the connector 100 may include another type of status flag, illustratively a single wire serial read/write non-volatile erasable, programmable read only memory (EPROM) 122, which may be programmed and subsequently read by a controller through port C to indicate that the lead set has been used. Other types of memory may be used as well, including single and multiple bit memory and Flash memory. Other types of devices may be used as well, including digital potentiometers.

FIGS. 9 and 10 show a connector 106 that incorporates both a serial read/write non-volatile EPROM 123 and a fuse 120. The EPROM 123 may be programmed with information to instruct a controller to burn out the fuse 120 after a preselected time period, or to generate a current spike to burn out the fuse 120 after expiration of a preselected time period. Other components shown in FIG. 10 include a resister 124 and a Zener diode 126.

FIG. 11 shows an illustrative mechanical mechanism that may be employed, in which a pin 128 is biased within port C. In operation, upon insertion of the connector 112 into a corresponding receptacle, the mechanism is actuated to release the biased pin 128. Upon removal of the connector 112 from the female receptacle, the released pin 128 prevents the connector from being reinserted into the female receptacle to prevent reuse.

The transcutaneous electrode and the percutaneous electrode may be implemented in any desired manner. While FIG. 2 shows a needle clip 28, for example, the lead may terminate in a needle without the intervening clip, or equivalents such as conductive tape may be used. An example of a suitable conductive tape is described in U.S. Patent Application Publication No. US 2005/0171576 published Aug. 4, 2005, which hereby is incorporated herein in its entirety by reference thereto. As described therein, a suitable tape member may have various layers sandwiched together, including a non-electrically conductive top layer, an intermediate electrically conductive foil layer, and a bottom electrically conductive adhesive layer. The opposing ends of the tape member are folded over onto each other and over the terminal end of the percutaneous needle electrode.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A lead set for a nerve stimulator having a one-way fit connection site, comprising:
a one-way fit plastic connector configured to mate with the one-way fit connection site;
a transcutaneous electrode;
a first lead extending from the connector and terminating in the transcutaneous electrode;
an attachment member for removably receiving a percutaneous needle electrode;
a second lead extending from the connector and terminating in the attachment member;
a fuse disposed entirely in the connector, said fuse including a functional status that is changeable during delivery of therapy after a pre-determined time period from an operational condition to a non-operational condition wherein the non-operational condition does not prevent continued delivery of said therapy;
a third lead disposed entirely in the connector and connected to the fuse; and
a fourth lead disposed entirely in the connector and connected to the fuse;
wherein the first lead and the second lead are electrically isolated from one another and physically separated at the transcutaneous electrode and the attachment member; and
wherein the fuse and the third and fourth leads are electrically isolated from both the first lead and the second lead; and
wherein the non-operational condition of the fuse is configured to prevent re-use of the lead set after delivery of the initial therapy.

2. A nerve stimulation kit for a nerve stimulator having a one-way fit connection site, comprising:
a percutaneous needle electrode; a
packaged alcohol pad; and
a lead set comprising:
 a one-way fit plastic connector configured to mate with the one-way fit connection site;
 a transcutaneous electrode;
 a first lead extending from the connector and terminating in the transcutaneous electrode;
 a needle clip for removably receiving the percutaneous needle electrode;
 a second lead extending from the connector and terminating in the needle clip;
 a fuse disposed entirely in the connector, said fuse including a functional status that is changeable during delivery of therapy after a pre-determined time period from an operational condition to a non-operational condition wherein the non-operational condition does not prevent continued delivery of therapy and is configured to prevent re-use of the lead set after delivery of the therapy;
 a third lead disposed entirely in the connector and connected to the fuse; and
 a fourth lead disposed entirely in the connector and connected to the fuse;
 wherein the first lead and the second lead are electrically isolated from one another and physically separated at the transcutaneous electrode and the needle clip; and
 wherein the fuse and the third and fourth leads are electrically isolated from both the first lead and the second lead.

3. A lead set comprising:
a first electrically conductive lead wire having a first end thereof and a transcutaneous electrode at a second end thereof;
a second electrically conductive lead wire having a first end thereof and an electrically conductive attachment member at a second end thereof, the attachment member being suspendable from a percutaneous needle electrode when inserted in a patient;
 a single-use mechanism comprising a fuse, said fuse including a functional status that is changeable during delivery of therapy to a patient after a pre-determined time period from an operational condition to a non-operational condition wherein the non-operational condition does not prevent continued delivery of therapy and is adapted to discourage or make difficult re-use of the lead set for electro-nerve stimulation after said delivery of the therapy;
 a connector, the first end of the first electrically conductive lead wire and the first end of the second electrically conductive lead wire being disposed in the connector.

4. A lead set for a nerve stimulator, comprising:
a keyed connector block having first, second, third and fourth conductors;
a first lead extending from the first conductor of the connector block and terminating in a patch electrode having adhesive on a surface thereof;
a second lead extending from the second conductor of the connector block and terminating in a needle clip; and
a fuse disposed in the connector block, the fuse being connected between the third and fourth conductors, said fuse including a functional status that is changeable during delivery of therapy after a pre-determined time period from an operational condition to a non-operational condition wherein the non-operational condition does not prevent continued delivery of therapy and is configured to prevent re-use of the lead set after delivery of the initial therapy.

5. The lead set of claim 4, wherein:
the patch electrode is permanently connected to the first lead; the needle clip is permanently connected to the second lead;
the first and second leads are merged in proximity to the connector block, and are separated away from the connector block; and
the connector block is plastic.

6. The lead set of claim 4, wherein the first lead is electrically isolated from the second lead and the fuse.

7. The lead set of claim 4, wherein the second lead is electrically isolated from the first lead and the fuse.

8. The lead set of claim 4, wherein:
the first lead is electrically isolated from the second lead and the fuse; and
the second lead is electrically isolated from the first lead and the fuse.

9. The lead set of claim 4, wherein the connector block is keyed to a connection site of a controller unit.

10. A lead set for a nerve stimulator, comprising:
a keyed connector block;
a first lead extending from a first port disposed in the connector block and terminating in a patch electrode;
a second lead extending from a second port disposed in the connector block and terminating in a needle clip; and
a fuse disposed in the connector block and electrically isolated from both the first lead and the second lead, the fuse being coupled between a third port and a fourth port disposed in the connector block, said fuse including a functional status that is changeable during delivery of therapy after a pre-determined time period from an operational condition to a non-operational condition wherein the non-operational condition does not prevent continued delivery of therapy and is configured to prevent re-use of the lead set after delivery of the therapy.

11. A lead set for a nerve stimulator, comprising:

a keyed connector block having first, second, third and fourth conductors;

a first lead extending from the first conductor of the connector block and terminating in a patch electrode having adhesive on a surface thereof;

a second lead extending from the second conductor of the connector block and terminating in a needle; and a fuse disposed in the connector block, the fuse being connected between the third and fourth conductors, said fuse including a functional status that is changeable during delivery of therapy after a pre-determined time period from an operational condition to a non-operational condition wherein the non-operational condition does not prevent continued delivery of therapy and is configured to prevent re-use of the lead set after delivery of the initial therapy.

12. The lead set of claim 11, wherein the first lead is electrically isolated from the second lead and the fuse.

13. The lead set of claim 11, wherein the second lead is electrically isolated from the first lead and the fuse.

14. The lead set of claim 11, wherein:

the first lead is electrically isolated from the second lead and the fuse; and the second lead is electrically isolated from the first lead and the fuse.

* * * * *